United States Patent [19]
Kräuter et al.

[11] Patent Number: 6,153,782
[45] Date of Patent: Nov. 28, 2000

[54] METHOD OF PRODUCING PROPYLSILANES

[75] Inventors: Thomas Kräuter, Homberg/Ohm; Steffen Seebald, Grosskrotzenburg; Christoph Batz-Sohn, Hanau; Ralf Karch, Kleinostheim; Matthias Prinz, Freigericht; Hermanus Gerhardus Jozef Lansink Rotgerink, Mömbris-Mensengesäss, all of Germany

[73] Assignee: Degussa-Hüls AG, Germany

[21] Appl. No.: 09/458,101

[22] Filed: Dec. 10, 1999

[30] Foreign Application Priority Data

Dec. 11, 1998 [DE] Germany .............. 198 57 223

[51] Int. Cl.[7] ............... C07F 7/08; C07F 7/10; C07F 7/18
[52] U.S. Cl. .......... 556/479; 556/413; 556/414; 556/415; 556/427; 556/445; 556/449
[58] Field of Search ............... 556/479, 414, 556/413, 427, 415, 445, 449

[56] References Cited

U.S. PATENT DOCUMENTS

| | | | |
|---|---|---|---|
| 3,714,212 | 1/1973 | Lengnick | 556/479 |
| 4,503,160 | 3/1985 | Williams | 556/479 X |
| 4,533,744 | 8/1985 | Williams | 556/479 |
| 5,177,236 | 1/1993 | Seller et al. | 556/479 |
| 5,296,595 | 3/1994 | Doyle et al. | 556/479 X |
| 5,347,027 | 9/1994 | Ritscher et al. | 556/413 |
| 5,559,264 | 9/1996 | Bowman et al. | 556/479 |
| 5,561,231 | 10/1996 | Dauth et al. | 556/479 X |
| 5,654,455 | 8/1997 | Pastor et al. | 556/479 X |

*Primary Examiner*—Paul F. Shaver
*Attorney, Agent, or Firm*—Pillsbury Madison & Sutro LLP

[57] ABSTRACT

A method for the production of organosilanes functionalized in 3-position by reacting suitable allyl compounds with hydrogen silanes in the presence of a multielement catalyst containing platinum and at least one other element.

5 Claims, No Drawings

METHOD OF PRODUCING PROPYLSILANES

CROSS-REFERENCE TO RELATED APPLICATION

This application claims priority from German Application No. 198 57 223.9, filed on Dec. 11, 1998, the subject matter of which is hereby incorporated herein by reference.

BACKGROUND OF THE INVENTION

1. Field of the Invention

The invention relates to a method of producing 3-functionalized propylsilanes from hydrogen silanes and allyl compounds.

2. Background Information

Hydrogen silanes such as, for example, trichlorosilane, can be reacted in the presence of allyl compounds with the aid of platinum-containing catalysts to yield 3-chloropropylsilane. This reaction is generally designated as hydrosilylation (see, e.g., equation I).

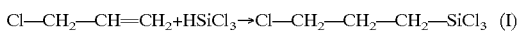
Cl—CH$_2$—CH=CH$_2$+HSiCl$_3$→Cl—CH$_2$—CH$_2$—CH$_2$—SiCl$_3$ (I)

The reaction can be carried out homogeneously or heterogeneously with platinum-containing catalysts. In the case of homogeneously catalyzed production, soluble platinum compounds, for example, H$_2$PtCl$_6$×6H$_2$O, are used as catalysts (DE-AS 19825793.7; DE-OS 28 51 456; CS 176 910; U.S. Pat. No. 4,292,433; U.S. Pat. No. 4,292,434; DE-AS 11 87 240; DE 11 65 028). For heterogeneous hydrosilylations, carriered platinum catalysts are used (U.S. Pat. No. 2,637,738; DE 20 12 299; DE 28 15 316).

It is known that in the reaction of, for example, allyl chloride with hydrogen silanes to 3-chloropropylsilanes, a part of the allyl chloride used reacts with the hydrogen silane in a side reaction to form propene and the particular chlorosilane (see, e.g., equation II).

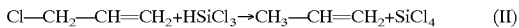
Cl—CH$_2$—CH=CH$_2$+HSiCl$_3$→CH$_3$—CH=CH$_2$+SiCl$_4$ (II)

During the reaction of allyl chloride with trichlorosilane, up to 25–30% of the allyl chloride used can be converted by this side reaction with trichlorosilane into propene and silicon tetrachloride. The molar ratio of chloropropylsilane to silicon tetrachloride in the raw product is a measure for the selectivity of the reaction and typically reaches values between 2.33:1 (70% yield relative to allyl chloride used) and 3:1 (75% yield).

It is furthermore known that the formation of propene can be reduced by a special reaction being carried out in pressure apparatuses; however, this method of operation has the consequence that the propene accumulating within the framework of the side reaction reacts further quantitatively with the hydrogen silane used to propylsilane. Even in the reactions carried out under normal pressure in the customary manner, the propene is converted to a considerable extent to the corresponding propylsilane (DE 34 04 703) (see, e.g., equation 3).

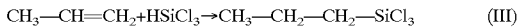
CH$_3$—CH=CH$_2$+HSiCl$_3$→CH$_3$—CH$_2$—CH$_2$—SiCl$_3$ (III)

Thus, up to 230 kg propyltrichlorosilane is obtained in an industrial system in a heterogeneous, catalytic reaction of allyl chloride and trichlorosilane in a column filled with a platinum-[/]activated-carbon catalyst per 1000 kg 3-chloropropyltrichlorosilane, which results in an additional requirement of approximately 28% trichlorosilane (DE 41 19 994). In addition to the additional requirement for trichlorosilane, further problems arise because of the difficult separation and expensive removal of the undesired propylsilanes.

SUMMARY OF THE INVENTION

It is an object of the invention to provide a method for the production of 3-functionalized propylsilanes which does not have these disadvantages.

The invention provides a method for the production of 3-functionalized propylsilanes by the addition of allyl compounds of the general formula IV

H$_2$C=CH—CH$_2$X (IV)

in which X can be =Cl, Br, I, F, CN, SCN, SH, SR, OH, NRR$^1$ or OR and R and R$^1$ signify, both independently of one another, (C$_1$–C$_6$) alkyl or (C$_3$–C$_7$) aryl
to silanes of the formula V

R$^2$R$^3$R$^4$SiH (V)

in which R$^2$, R$^3$, R$^4$ can signify, all independently of each other, hydrogen, halogen, (C$_1$–C$_6$) allyl, (C$_1$–C$_4$) alkoxy, phenyl, aryl or aralkyl at reaction temperatures between 0° C. and 200° C. and pressures between 200 mbar and 10 bar and in the presence of a catalyst, which is characterized in that the catalyst is a carriered multielement catalyst of which one element is platinum. It is preferred that X be a halogen, especially chlorine.

Trichlorosilane, methylhydrogen dichlorosilane, propylhydrogen dichlorosilane of dimethylhydrogen chlorosilane can be used as the silane of formula V.

The use of the catalyst in the method of the invention is possible at normal, excess or reduced pressure. The process is preferably carried out at pressures between 200 mbar and 10 bar, especially at 800 mbar to 6 bar. A pressure between 800 mbar and 2 bar is especially preferred.

The use of the catalyst in the method of the invention can take place in a batch method, that is, that the allyl compound and the hydrogen silane used in an excess are brought to a reaction in a suitable container together with the catalyst at temperatures between 0° C. and 200° C. and pressures between 200 mbar and 10 bar until all the allyl chloride has been reacted. Alternatively, the catalyst can be used in a continuous method. It is filled into a reactor and a mixture of the allyl compound and the hydrogen silane used in an excess is allowed to flow over it at temperatures between 0° C. and 200° C. and pressures between 200 mbar and 10 bar; the reaction to the corresponding chloropropylsilane takes place thereby.

The catalyst in the method of the invention contains a carrier, platinum and at least one further element.

All current materials such as carbons, silicates and metal oxides can be considered as carrier materials. Examples for carriers are activated carbons, cokes and graphites, zeolites and mesoporous materials, Deloxanes®, carbides and inorganic oxides such as silicon dioxide, aluminum oxide, silicates, titanium dioxide and zirconium oxide. Activated carbons are especially preferred as carrier materials. The carrier materials can be present as granulate, extrudate, spheres or in other customary forms. The catalyst can be produced by impregnation, adsorption, saturation or precipitation of the active components onto the carrier.

The platinum component used can be inorganic platinum compounds, for example, hexachloroplatinic acid, platinum nitrate, platinum tetramine chloride, platinum tetramine nitrate, platinum acetate, platinum tetramine carbonate, platinum sulfite acid liquor, platinum oxyhydrate as well as organic and/or metalorganic platinum compounds, for example, methylethanolamine hexahydroxoplatinate, platinum tetrakis (triphenylphosphane), platinum acetylacetonate. The production of platinum compounds in general is described in "Gmelins Handbuch der Anorganischen Chemie" [German="Gmelin's Handbook of Inorganic Chemistry"], $8^{th}$ edition, volume 68. The platinum-containing compounds can be applied onto the carrier individually or in any mixtures. The concentration of the platinum on the carrier can be 0.05 to 10% by weight, preferably 0.2 to 5%, relative to the carrier. The platinum can be present in ionic form or elementary form on the carrier.

Further elements of the catalyst which can be applied onto the carrier are titanium, zirconium, hafnium, vanadium, chromium, molybdenum, tungsten, manganese, rhenium, iron, ruthenium, osmium, cobalt, rhodium, iridium, nickel, copper, silver, gold, zinc, aluminum, gallium, indium, tin, lead, antimony, bismuth, samarium and/or sulfur. Titanium, iron, ruthenium, cobalt, rhodium, iridium, nickel, palladium, aluminum, indium, tin and/or sulfur are used with preference. Aluminum, indium and sulfur are especially preferred. The elements can be applied individually or in any combinations in addition to the platinum.

The metals used in addition to the platinum are applied as aqueous or alcoholic solutions of their inorganic salts, for example, as palladium nitrate, ruthenium chloride, rhodium chloride, indium nitrate, aluminum nitrate, bismuth oxide or cobalt chloride. The application of the metal components can take place in a concerted manner as well as sequentially in any sequence for applying the platinum component. The metal compounds are reduced on the carrier with hydrogen at temperatures above 400° C. This type of reduction is not used if one of the applied elements is sulfur.

Sulfur is applied onto the carrier as a sulfur-containing compound. The sulfur-containing component can be a sulfate, sulfite, sulfide, sulfoxide, sulfane, polysulfane or thiol or, in general, sulfur compounds in which the sulfur is present in the formal oxidation stages of −2 to +6. Examples of this are, in particular, dimethylsulfoxide, dimethylsulfide, thiourea, thioacetamide, sodium sulfide and tetrahydrothiophene. The sulfur-containing compounds can be used individually or in any mixtures.

Organometallic platinum compounds which have one or several sulfur-containing, organic groups on the platinum atom can also be used as sulfur-containing component, for example, $(THT)_2PtCl_2$ (THT=tetrahydrothiophene, E. G. Cox et al., J. Chem. Soc. A (1934), 182), $(DMSO)_2 PtCl_2$ (DMSO=dimethylsulfoxide, J. H. Pierce et al., Inorg. Chem. 11 (1982) or $(Et_2S)_2PtCl_2$, (E. G. Cox et al., J. Chem. Soc. A (1934), 182).

The application of the sulfur-containing platinum component on the carrier takes place according to known methods in the literature (C. N. Satterfield, Heterogeneous Catalysis in Practice, McGraw-Hill Book Company, New York 1980, 68 ff; J. Hagen, Technische Katalyse [German= Industrial Catalysis], VCH Verlag, Weinheim 1996, 87 ff; J. Falbe, U. Hasserodt, Katalysatoren, Tenside und Mineral öladditive [German=Catalysts, Surfactants and Mineral-Oil Additives], Georg Thieme Verlag, Stuttgart 1978, 7 ff). The application of the sulfur-containing component onto the carrier can take place prior to the use in the hydrosilylation reaction or during the reaction with the educt mixture (in situ). The sulfur-containing platinum component can be reduced after being applied to the carrier or be left in the oxidative form.

The molar ratio between platinum and the other elements on the carrier can be 0.001:1 to 100:1, preferably 0.01:50:1 and especially preferably 0.05:1 to :20:1. The total amount of platinum and of the other elements on the carrier is 0.01 to 20% by weight, preferably 0.1 to 10% by weight.

DETAILED DESCRIPTION OF THE INVENTION

The following examples 1 to 6 demonstrate in an exemplary manner the production of the catalysts. Examples 7 and 8 serve as reference examples. The use of the catalysts in the method of the invention is described in examples 9 to 14. Examples 15, 16 also serve as reference examples here. The indication of selectivity signifies thereby the molar ratio between the desired product 3-chloropropyltrichlorosilane (Cl-PTS) and silicon tetrachloride. The examples in accordance with the invention demonstrate by the selectivities achieved and by the yields of 3-chloropropyltrichlorosilane the superiority of these catalysts over traditional, heterogeneous catalysts in the method of the invention.

EXAMPLE 1

99.0 g activated carbon is covered with an aqueous solution of 2.1 g hexachloroplatinic acid in a 1 l PE container and dried at 100° C. in a current of air. The material is subsequently reduced at 400° C. with an $H_2/N_2$ gaseous mixture (5% $H_2$), washed with water and dried 12 h at 120° C. in a vacuum drying oven.

An aqueous solution with 3.23 g dimethylsulfoxide and subsequently an aqueous solution with 1.55 g hydrazine are added to the dry material. The concluding drying takes place at 105° C.

EXAMPLE 2

99.0 g activated carbon is covered with an aqueous solution of 2.1 g hexachloroplatinic acid and 2.42 g dimethylsulfoxide in a 1 l PE container and dried at 100° C. in a current of air. The material is subsequently reduced in an aqueous hydrazine solution with 10.33 g hydrazine. The material is subsequently washed with water and dried 12 h at 105° C. in a vacuum drying oven.

EXAMPLE 3

99.0 g activated carbon is covered with an aqueous solution of 2.1 g hexachloroplatinic acid and 3.23 g dimethylsulfoxide in a 1 l PE container and dried at 100° C. in a current of air. The material is subsequently reduced in an aqueous hydrazine solution with 12.92 g hydrazine. The material is subsequently washed with water and dried 12 h at 105° C. in a vacuum drying oven.

EXAMPLE 4

99.0 g activated carbon is covered with an aqueous solution of 1.85 g hexachloroplatinic acid and 1.14 g aluminum nitrate nonahydrate in a 1 l PE container and dried at 100° C. in a current of air. The material is subsequently reduced at 600° C. with an $H_2/N_2$ gaseous mixture (5% $H_2$), washed with water and dried 12 h at 120° C. in a vacuum drying oven.

EXAMPLE 5

99.0 g activated carbon is covered with an aqueous solution of 1.32 g hexachloroplatinic acid and 1.14 g indium nitrate in a 1 l PE container and dried at 100° C. in a current of air. The material is subsequently reduced at 500° C. with an $H_2/N_2$ gaseous mixture (5% $H_2$), washed with water and dried 12 h at 120° C. in a vacuum drying oven.

EXAMPLE 6

99.0 g activated carbon is covered with an aqueous solution of 1.32 g hexachloroplatinic acid and 1.14 g indium nitrate in a 1 l PE container and dried at 100° C. in a current of air. The material is subsequently reduced at 600° C. with an $H_2/N_2$ gaseous mixture (5% $H_2$), washed with water and dried 12 h at 120° C. in a vacuum drying oven.

EXAMPLE 7 (REFERENCE EXAMPLE)

99.0 g activated carbon is covered with an aqueous solution of 2.1 g hexachloroplatinic acid in a 1 l PE container and dried at 100° C. in a current of air. The material is subsequently reduced at 400° C. with an $H_2/N_2$ gaseous mixture (5% $H_2$), washed with water and dried 12 h at 120° C. in a vacuum drying oven.

EXAMPLE 8 (REFERENCE EXAMPLE)

99.0 g activated carbon is covered with an aqueous solution of 2.1 g hexachloroplatinic acid in a 1 l PE container and dried at 100° C. in a current of air. The material is subsequently reduced in an aqueous hydrazine solution with 2.56 g hydrazine. The material is subsequently washed with water and dried 12 h at 120° C. in a vacuum drying oven.

EXAMPLE 9

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst of the invention from example 1 to a boil. During the course of the reaction the internal temperature rises from approximately 40° C. to approximately 110° C. due to the conversion of the low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off the following product composition results:
1.71% by weight trichlorosilane (TCS)
0.07% by weight allyl chloride (ACl)
20.58% by weight silicon tetrachloride (STC)
1.12% by weight propyltrichlorosilane (PTS)
76.03% by weight 3-chloropropyltrichlorosilane (Cl-PTS).

Thus, a value of 2.96:1 results for the selectivity of the reaction relative to the amounts of substance, which corresponds to a yield of 3-chloropropyltrichlorosilane relative to allyl chloride of 747%.

EXAMPLE 10

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst of the invention from example 2 to a boil. During the course of the reaction the internal temperature rises from approximately 40° C. to approximately 110° C. due to the conversion of the low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off, the following product composition results:
0.82% by weight trichlorosilane (TCS)
0.26% by weight allyl chloride (ACl)
20.18% by weight silicon tetrachloride (STC)
1.15% by weight propyltrichlorosilane (PTS)
76.96% by weight 3-chloropropyltrichlorosilane (Cl-PTS).

Thus, a value of 3.06:1 results for the selectivity of the reaction relative to the amounts of substance, which corresponds to a yield of 3-chloropropyltrichlorosilane relative to allyl chloride of 75.4%.

EXAMPLE 11

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst of the invention from example 3 to a boil. During the course of the reaction the internal temperature rises from approximately 40° C. to approximately 110° C. due to the conversion of low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off, the following product composition results:
0.66% by weight trichlorosilane (TCS)
0.40% by weight allyl chloride (ACl)
20.31% by weight silicon tetrachloride (STC)
1.03% by weight propyltrichlorosilane (PTS)
76.92% by weight 3-chloropropyltrichlorosilane (Cl-PTS).

Thus, a value of 3.04:1 results for the selectivity of the reaction relative to the amounts of substance, which corresponds to a yield of 3-chloropropyltrichlorosilane relative to allyl chloride of 75.2%.

EXAMPLE 12

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst of the invention from example 4 to a boil. During the course of the reaction the internal temperature rises from approximately 40° C. to approximately 110° C. due to the conversion of low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off, the following product composition results:
2.56% by weight trichlorosilane (TCS)
1.34% by weight allyl chloride (ACl)
19.55% by weight silicon tetrachloride (STC)
2.76% by weight propyltrichlorosilane (PTS)
73.79% by weight 3-chloropropyltrichlorosilane (Cl-PTS).

Thus, a value of 3.03 results for the selectivity of the reaction relative to the amounts of substance, which corresponds to a yield of 3-chloropropyltrichlorosilane relative to allyl chloride of 75.2%.

EXAMPLE 13

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst of the invention from example 5 to a boil. During the course of the reaction the internal temperature rises from approximately 40° C. to approximately 110° C. due to the conversion of the low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off the following product composition results:
3.13% by weight trichlorosilane (TCS)
1.21% by weight allyl chloride (ACl)
18.75% by weight silicon tetrachloride (STC)
2.40% by weight propyltrichlorosilane (PTS)
74.51% by weight 3-chloropropyltrichlorosilane (Cl-PTS).

Thus, a value of 3.19:1 results for the selectivity of the reaction relative to the amounts of substance, which corresponds to a yield of 3-chloropropyltrichlorosilane relative to allyl chloride of 76.1%.

EXAMPLE 14

100 g (472 mmol) 3-chloropropyltrichlorosilane, 76.6 g (1.0 mol) ally chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst of the invention from example 6 to a boil. During the course of the reaction the internal temperature rises from approximately 40° C. to approximately 110° C. due to the conversion of the low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off, the following product composition results:
2.45% by weight trichlorosilane (TCS)
0.75% by weight allyl chloride (ACl)
19.15% by weight silicon tetrachloride (STC)
2.37% by weight propyltrichlorosilane (PTS)
75.27% by weight 3-chloropropyltrichlorosilane (Cl-PTS).

Thus, a value of 3.15:1 results for the selectivity of the reaction relative to the amounts of substance, which corresponds to a yield of 3-chloropropyltrichlorosilane relative to allyl chloride of 75.9%.

EXAMPLE 15 (COMPARATIVE EXAMPLE)

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst from example 7 to a boil. During the course of the reaction the internal temperature rises from approximately 40° C. to approximately 110° C. due to the conversion of low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off, the following product composition results:
25.47% by weight trichlorosilane (TCS)
1.83% by weight allyl chloride (ACl)
19.89% by weight silicon tetrachloride (STC)
3.41% by weight propyltrichlorosilane (PTS)
49.39% by weight 3-chloropropyltrichlorosilane (Cl-PTS).

Thus, a value of 2.48:1 results for the selectivity of the reaction relative to the amounts of substance, which corresponds to a yield of 3-chloropropyltrichlorosilane relative to allyl chloride of 71.3%.

EXAMPLE 16 (COMPARATIVE EXAMPLE)

100 g (472 mmol) 3-chloropropyltrichlorosilane, 76.6 g (1.0 mol) allyl chloride and 142.3 g (1.05 mol) trichlorosilane are mixed in a 500 ml three-neck flask with heating mantle, magnetic agitator, internal thermometer and a reflux condenser intensively cooled to −30° C. and are heated in the presence of 2.0 g of the catalyst from example 8 to a boil. During the course of the reaction the internal temperature rises from approximately 40° C. to approximately 110° C. due to the conversion of low-boiling components to higher-boiling products. The reaction is terminated when the boiling temperature remains constant at a high level for an extended time. The mixture is cooled off thereafter and the production mixture produced is examined by gas chromatography. After the 3-chloropropyltrichlorosilane used as solvent has condensed off, the following product composition results:
9.36% by weight trichlorosilane (TCS)
5.86% by weight allyl chloride (ACl)
20.02% by weight silicon tetrachloride (STC)
3.67% by weight propyltrichlorosilane (PTS)
60.27% by weight 3-chloropropyltrichlorosilane (Cl-PTS).

Thus, a value of 2.41:1 results for the selectivity of the reaction relative to the amounts of substance, which corresponds to a yield of 3-chloropropyltrichlorosilane relative to allyl chloride of 70.7%.

Publications cited herein are hereby incorporated by reference.

What is claimed is:

1. A method for the production of 3-functionalized propylsilanes by the addition of allyl compounds of the general formula IV $$H_2C=CH-CH_2X \qquad (IV)$$

in which X is Cl, Br, I, F, CN, SCN, SH, SR, OH, NRR$^1$ or OR and R and R$^1$ signify, both independently of one another, ($C_1-C_6$) alkyl or ($C_3-C_7$) aryl to silanes of the formula V $$R^2R^3R^4SiH \qquad (V)$$

in which $R^2$, $R^3$, $R^4$ signify, independently of each other, hydrogen, halogen, ($C_1-C_6$) allyl, ($C_1-C_4$) alkoxy, phenyl, aryl or aralkyl, at reaction temperatures between 0° C. and 200° C. and pressures between 200 mbar and 10 bar and in the presence of a catalyst, wherein the catalyst is a carriered multielement catalyst of which one element is platinum.

2. The method according to claim 1, wherein other elements of the catalyst are titanium, zirconium, hafnium, vanadium, chromium, molybdenum, tungsten, manganese, rhenium, iron, ruthenium, osmium, cobalt, rhodium, iridium, nickel, copper, silver, gold, zinc, aluminum, gallium, indium, tin, lead, antimony, bismuth, samarium and/or sulfur.

3. The method according to claim 1, wherein trichlorosilane, methylhydrogen dichlorosilane, propylhydrogen dichlorosilane or dimethylhydrogen chlorosilane is used as silane of formula V.

4. The method according to claim 1, wherein the carrier is activated carbon, coke or graphite, zeolite, Deloxane, carbide or inorganic oxide such as silicon dioxide, aluminum oxide, silicate, titanium dioxide or zirconium oxide.

5. The method according to claim 1, wherein the platinum component is an inorganic, organic or organometallic platinum compound.

* * * * *